United States Patent
Koski

(10) Patent No.: US 11,872,254 B2
(45) Date of Patent: Jan. 16, 2024

(54) METHODS FOR COLONIZING WITH BENEFICIAL ORAL BACTERIA

(71) Applicant: ProBiora Health, LLC, Dallas, TX (US)

(72) Inventor: Christine Koski, Dallas, TX (US)

(73) Assignee: ProBiora Health, LLC, Dallas, TX (US)

( * ) Notice: Subject to any disclaimer, the term of this patent is extended or adjusted under 35 U.S.C. 154(b) by 112 days.

(21) Appl. No.: 17/477,380

(22) Filed: Sep. 16, 2021

(65) Prior Publication Data

US 2022/0000945 A1   Jan. 6, 2022

Related U.S. Application Data

(62) Division of application No. 16/036,764, filed on Jul. 16, 2018, now Pat. No. 11,147,845.

(51) Int. Cl.
| | |
|---|---|
| *A01N 63/00* | (2020.01) |
| *A61K 35/744* | (2015.01) |
| *A61K 9/00* | (2006.01) |
| *A61K 35/747* | (2015.01) |
| *A23L 33/135* | (2016.01) |
| *A61K 35/745* | (2015.01) |
| *A61K 35/00* | (2006.01) |

(52) U.S. Cl.
CPC .......... *A61K 35/744* (2013.01); *A23L 33/135* (2016.08); *A61K 9/006* (2013.01); *A61K 35/745* (2013.01); *A61K 35/747* (2013.01); *A23V 2002/00* (2013.01); *A23V 2400/237* (2023.08); *A61K 2035/115* (2013.01)

(58) Field of Classification Search
CPC .................................................. A61K 35/744
See application file for complete search history.

(56) References Cited

U.S. PATENT DOCUMENTS

| | | |
|---|---|---|
| 7,674,613 B2 | 3/2010 | Koga |
| 2007/0098847 A1 | 5/2007 | Teissier |
| 2009/0311199 A1 | 12/2009 | Hillman |
| 2010/0047190 A1 | 2/2010 | Reindl et al. |
| 2011/0086236 A1 | 4/2011 | Catchmark et al. |
| 2015/0335577 A1 | 11/2015 | Agueros Bazo et al. |

*Primary Examiner* — Albert M Navarro
(74) *Attorney, Agent, or Firm* — Fish IP Law, LLP

(57) ABSTRACT

Methods are provided for controlled release of stabilized bacteria into the oral cavity on consumption of a food, candy, gum, or similar substance so as to promote colonization of oral surface by the bacteria. Bacteria are selected to treat an oral condition, such as oral disease, halitosis, and/or stained enamel on consumption of the food.

6 Claims, 3 Drawing Sheets

METHODS FOR COLONIZING WITH BENEFICIAL ORAL BACTERIA

This application is a divisional application of U.S. patent application Ser. No. 16/036,764 filed on Jul. 16, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is compositions and methods for introducing probiotic bacterial compositions to the mouth and/or gastrointestinal tract.

BACKGROUND

The following description includes information that may be useful in understanding the present invention. It is not an admission that any of the information provided herein is prior art or relevant to the presently claimed invention, or that any publication specifically or implicitly referenced is prior art.

Tooth surfaces are porous and can become stained or discolored by the use of tobacco products, eating or drinking certain foods and beverages (e.g., coffee, tea and red wine), the buildup of dental plaque, the process of aging, diseases, trauma, medications, congenital conditions, and other environmental effects. Teeth are comprised of an inner dentin layer, an outer enamel layer and an acquired pellicle. The acquired pellicle is a proteinaceous layer derived from saliva that forms on the surface of tooth enamel.

Extrinsic and intrinsic staining of the teeth can occur. Extrinsic staining is staining of the acquired pellicle that can occur when compounds such as tannins and polyphenolic compounds come in contact with teeth during eating, drinking or smoking. These compounds then become trapped in and tightly bound to the proteinaceous layer on the surface of the teeth. Extrinsic staining can be removed by mechanical methods of tooth cleaning, such as brushing or flossing and by chemical cleaning methods. Even with regular brushing and flossing, rapid or slow accumulation can develop into noticeable intrinsic tooth discoloration. Intrinsic staining can be caused by staining compounds that penetrate the enamel layer and the dentin layer or can arise from sources within the tooth. Intrinsic staining is difficult to remove and cannot typically be removed by mechanical methods of tooth cleaning, but high chemical concentrations and/or prolonged chemical cleaning methods can be used to remove some or all of this type of staining.

White, unstained teeth are considered cosmetically desirable. Teeth can be whitened by, for example, mechanical cleaning methods, veneers that are placed over the teeth, and chemical bleaching.

While tooth whitening products are known in the art, these products are traditionally used by those seeking the cosmetic benefit of whiter teeth. However, there is a different population of consumers who desire whiter teeth and/or more oral benefits including cleaner teeth, healthier gums, and decreased oral malodor. Therefore, there is a desire to provide oral hygiene products that can deliver oral care benefits in addition to tooth whitening. Furthermore, oral hygiene time is typically limited and so there is a desire to deliver these oral care benefits quickly and conveniently as part of a daily oral hygiene regimen.

U.S. Pat. No. 7,674,613, to Koga, describes foods that include a dried preparation of *Lactobacillus salivarius* that has been selected to suppress the growth of periodontopathic and cariogenic bacteria. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Such an approach, however, is unlikely to be effective when applied to bacteria that are relatively labile and/or moisture sensitive while in a lyophilized or dry state. This reduction in soluble protein concentrations reduces the production of malodorous compounds in the mouth. United States Patent Application Publication No. 2010/0047190, to Reindl et al, describes the use of lactic acid bacteria selected to bind to and aggregate *Streptococcus mutans* and that can be administered in a food, liquid, or film. Since no particular measures are taken to protect the viability of these bacteria, however, it is not clear if this approach can be successful with more labile species. This aggregation apparently reduces the incidence of dental caries. Since no particular measures are taken to protect the viability of these bacteria, however, it is not clear if this approach can be successful with more labile species. United States Patent Application Publication No. 2015/0335577, to Agüeros Bazo et al, describes microencapsulation of probiotic bacteria mixtures using casein and chitosan, which provides protection for the microencapsulated bacteria until they reach the gut. United States Patent Application Publication No. 2007/0098847, to Teissier, describes the use of dehydrated and granulated "lactic bacteria" that has been coated with a solid vegetable fat in foods, which provides protection from moisture and release in the gut. Such methods, however, are not suitable for delivery of labile bacteria species to the oral cavity.

Thus, there is still a need for convenient and palatable means for introducing labile bacteria to the oral cavity.

SUMMARY OF THE INVENTION

The inventive subject matter provides compositions and methods in which probiotic bacteria are released into the oral cavity through consumption of a foodstuff or application of a mucosal patch. Consumption of the foodstuff or application of the mucosal patch provides release of probiotic bacteria for a time sufficient to at least transiently colonize surfaces within the oral cavity, displacing potentially harmful bacterial species.

One embodiment of the inventive concept is food substance (such as a chewing gum, a hard candy, a wafer, a sprinkle, and/or a breath mint) that includes a stabilized bacterial formulation. The stabilized bacterial formulation includes a stabilized non-pathogenic, hydrogen peroxide bacterial species or strain and a genetically modified LDH-deficient bacterial strain, and is provided in a solid or semi-solid consumable vehicle. The stabilized bacterial formulation can include lyophilized bacteria and/or encapsulated bacteria. Such encapsulated bacteria can include a matrix compound, for example casein, starch, a chitosan, and/or an edible wax or oil. In such an embodiment the edible wax or oil can have a melting point of greater than 35° C. The stabilized bacterial formulation can include a stabilizer selected to improve stability of the stabilized bacterial formulation. Suitable hydrogen peroxide-producing bacterial species or strains include *Lactobacillus*, Bifidobacteria, *viridans Streptococcus, Leuconostoc, Pediococcus*, and *Lactococcus*. Suitable genetically modified LDH-deficient bacterial strains include genetically modified strains of *Streptococcus mutans*.

Another embodiment of the inventive concept is a mucosal patch that includes a support layer and a film layer. The film layer has a first surface that is coupled to the support layer, and includes a stabilized bacterial formulation. The stabilized bacterial formulation includes isolated, non-pathogenic, hydrogen peroxide bacterial species or strains and genetically modified LDH-deficient bacterial strains. Such bacterial strains can be lyophilized and/or encapsulated (for example, within a matrix of casein, starch, a chitosan, and/or an edible wax or oil). Edible waxes or oils utilized can have a melting point in excess of 35° C. The support layer is sized to fit within a human oral cavity, and can include an adhesive. In some embodiments the mucosal patch also includes a barrier layer that is attached to a second surface of the film layer in a reversible fashion.

Another embodiment of the inventive concept is a method of colonizing an oral cavity with probiotic bacteria by providing a food substance (for example, chewing gum, a hard candy, a wafer, and/or a breath mint) that includes a stabilized bacterial formulation. The stabilized bacterial formulation includes an isolated, non-pathogenic, hydrogen peroxide bacterial species or strain and a genetically modified LDH-deficient bacterial strain. Suitable hydrogen peroxide-producing bacterial species or strain include *Lactobacillus*, Bifidobacteria, *viridans Streptococcus, Leuconostoc, Pediococcus*, and *Lactococcus*. Suitable genetically modified LDH-deficient bacterial strain include genetically modified strains of *Streptococcus mutans*. The food substance is retained within the oral cavity for at least 30 seconds. The probiotic bacteria can be stabilized, for example by drying (e.g. lyophilization) and/or encapsulation. Encapsulated preparation can include a matrix compound, such as casein, starch, a chitosan, and/or an edible wax or oil (for example, and edible wax or oil with a melting point in excess of about 35° C.). Instructions can be provided for consumption of the food substance.

Another embodiment of the inventive concept is a method of at least transiently colonizing an oral cavity with probiotic bacteria by providing a mucosal patch that includes a support layer, and also includes a film layer comprising a first surface coupled to the support layer. The film layer includes a stabilized bacterial formulation, which in turn includes isolated, non-pathogenic, hydrogen peroxide bacterial species or strains and genetically modified LDH-deficient bacterial strains. The film layer is placed in contact with a mucosal surface of the oral cavity, and is retained in the oral cavity for a time sufficient to release at least a portion of the stabilized bacterial formulation into the oral cavity. The bacterial formulation can lyophilized and/or encapsulated bacteria. Such encapsulated bacteria can include a matrix compound such as casein, starch, a chitosan, and/or an edible wax or oil (or example, and edible wax or oil that melts at temperatures in excess of 35° C.). The mucosal patch can also include a barrier layer that is reversibly attached to a second surface of the film layer. In such embodiments the barrier layer is removed prior to placing the film layer in contact with the mucosal surface.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A shows such an embodiments in which the shell is essentially homogeneous. FIG. 1B shows such an embodiment in which the shell has inclusions that assist in breakdown in the oral cavity.

DETAILED DESCRIPTION

Figure 1A:
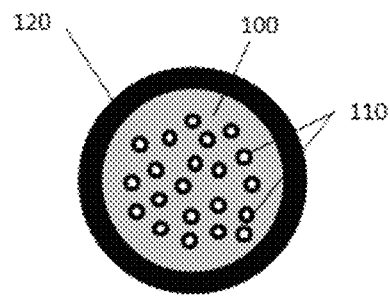
FIGS. 1A and 1B schematically depict embodiments of the inventive concept in which a stabilized bacterial preparation is suspended within a rigid, protective shell.

Compositions and methods of the inventive concept provide protection of a labile (e.g. moisture sensitive) bacterial preparation for delivery into the oral cavity using a packaging or matrix that provides protection from water/humidity when intact but that releases readily in the mouth when consumed as or as part of a foodstuff. Labile bacterial preparations, such as lyophilized or otherwise dried bacterial preparations that include a lactate dehydrogenase-deficient (LDH-deficient) *mutans streptococcus*, are thereby protected from moisture prior to storage but are released into the oral cavity over a period of time when consumed. One should appreciate that compositions and methods provide oral delivery of labile probiotic bacterial preparations, under conditions which can provide for at least transient colonization of surfaces within the oral cavity (such as teeth and/or gums). Such colonization can provide competition for bacteria responsible for dental caries and other oral conditions, and can provide compounds that improve the appearance of discolored teeth (such as peroxides).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The instant invention provides methods and compositions that provide for at least transient colonization of the oral cavity by beneficial bacteria, which can act to displace oral bacteria that can cause various unwanted oral conditions (for example, acid elaborating bacteria that break down tooth enamel, etc.). Such displacement can provide maintenance or improvement of oral health, including, for example, tooth whitening. A composition of the invention comprises a stabilized probiotic bacterial composition that includes one or more isolated, non-pathogenic, hydrogen peroxide-producing species or strains of bacteria, and optionally, LDH-deficient *mutans Streptococcus*. Certain bacteria can produce hydrogen peroxide at a level that can whiten teeth as demonstrated herein for the first time. A composition of the invention can influence or effect a desired change in appearance and/or structure of a tooth surface. Examples of appearance and structural changes include, but are not necessarily limited to, whitening, stain bleaching, stain removal, plaque removal, and tartar removal. Furthermore, a composition of the invention can provide additional oral care benefits such as displacement of bacteria that can cause dental caries, periodontitis, oral bacterial infections and diseases, oral wounds, *Candida* or fungal overgrowth, halitosis, or xerostomia-induced dental caries and associated periodontal diseases, or a combination thereof to a subject.

Another embodiment of the inventive concept is a method for reducing staining or discoloration of tooth surfaces using a composition comprising one or more non-pathogenic, hydrogen peroxide-producing *viridans* Streptococci species or strains, and/or one or more non-pathogenic, hydrogen peroxide-producing *Lactobacillus* species or strains and/or one or more non-pathogenic, hydrogen peroxide-producing Bifidobacteria species or strains and/or one or more non-pathogenic, hydrogen peroxide producing *Lactococcus* species or strains and/or one or more non-pathogenic, hydrogen peroxide producing *Pediococcus* species or strains and/or one or more non-pathogenic, hydrogen peroxide producing *Leuconostoc* species or strains. In one embodiment of the invention the bacterial strains can be generally recognized as safe (GRAS), and can transiently attach or adhere to a tooth surface by virtue of electrostatic interactions, van der Waals interactions, or protein or polysaccharide adhesins on the bacterial surface that recognize and interact with molecules present on the tooth surface. Examples of *viridans* Streptococci species include, but are not limited to *S. sanguis, S. parasanguis, S. gordonii, S. oralis, S. uberis, S. mitis, S. rattus, S. salivariaus, S. vestibularis, S. angionosus, S. constellatus, S. intermedius, S. mutans, S. sobrinus, S. milleri, S. cricetus,* and *S. mitior*. Examples of *Lactobacillus* species include, but are not limited to, *L. acidophilus, L. jensenii, L. catenaforme, L. leichmanni, L. plantarum, L. johnsonii, L. gasseri, L. delbrueckii, L. casei, L. brevis, L. salivarius, L. gasseri, L. sobrius, L. rhamnosus, L. reuteri, L. fermentum, L. paracasei, L. dextranicum,* and *L. helveticus*. Examples of Bifidobacteria species include, but are not limited to *B. angulatum, B. animalis, B. asteroides, B. bifidum, B. boum, B. breve, B. catenulatum, B. choerinum, B. coryneforme, B. cuniculi, B. dentium, B. gallicum, B. gallinarum, B. indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum,* and *B. urinali*. Examples of other non-pathogenic bacteria that can produce hydrogen peroxide include, without limitation, *Pediococcus* species, such as *P. acidilactici, Leuconostoc* species, such as *L. mesenteroides,* and *Lactococcus* species such as *L. lactis*.

The quantity of hydrogen peroxide produced by bacteria can be experimentally determined. See e.g. Hillman and Shivers, Arch. Oral. Biol., 33:395-401 (1988). The culture liquor of cells grown in the presence of oxygen is incubated with 40 µh/ml horseradish peroxidase and 0.4 µmol/ml o-dianisidine. After 2 minutes, the reaction is stopped by the addition of 0.02 ml of 5N HCl. The optical density of the sample is measured at 410 nm and the hydrogen peroxide concentration of the sample is calculated from a standard curve prepared using authentic hydrogen peroxide and an extinction coefficient at 230 nm of 81M−1 cm-1. In one embodiment of the invention the bacteria can produce at least about 0.5, 1, 2, 5 mM or more of $H_2O_2$ or any range or value between about 0.1 and about 5 mM.

In one embodiment of the invention a composition of the invention comprises one or more isolated *Streptococcus oralis* strains and/or one or more *S. uberis* strains. Compositions of the invention can optionally comprise one or more isolated strains or species of *mutans streptococcus* that are LDH-deficient. The combination of non-pathogenic, hydrogen peroxide-producing bacteria and/or *mutans streptococcus* provides a significant practical advantage in that the combination can used to reduce oral populations of organisms responsible for dental caries, periodontitis, oral bacterial infections and diseases, oral wounds, *Candida* or fungal overgrowth, halitosis, or xerostomia-induced dental caries or periodontal disease, while also whitening the teeth.

*Streptococcus oralis* (previously known as *S. sanguis* Type II) and *S. uberis* are important components in maintaining the normal, healthy balance of microorganisms that comprise the periodontal flora. See Socransky et al., Oral Microbiol. Immunol. 3:1-7 (1988); Hillman and Shivers, Arch. Oral. Biol., 33:395-401 (1988); Hillman et al., Arch. Oral. Biol., 30:791-795 (1985). *S. oralis* can also be found in dental plaque and has been demonstrated to correlate with periodontal health, in particular by interfering with the colonization by periodontal pathogens such as Aggregetobacter *actinomycetemcomitans, Porphyromonas gingivalis, Peptostreptococcus micros*, and *Campylobacter* rectus. Compositions of the invention can comprise one or more isolated strains of *S. oralis*, for example, ATCC 35037, ATCC 55229, ATCC 700233, ATCC 700234 and ATCC 9811. Other strains of *S. oralis* include KJ3 and KJ3sm. KJ3sm is a naturally occurring genetic variant of KJ3 that is resistant to 1 mg/ml streptomycin. The streptomycin resistance is advantageous because it provides a marker for easy isolation of the bacteria. Additionally, streptomycin resistant strains are slightly attenuated and do not survive as long in an oral cavity as wild-type strains. This property is useful where the goal is to non-persistently colonize the oral cavity of an animal with the bacteria.

*S. uberis* can also be found in dental plaque and has been demonstrated to correlate with periodontal health, in particular by interfering with the colonization by periodontal pathogens such as *Tannerella forsythensis, P. micros, C. rectus*, and *Prevotella melaninogenica*. Compositions of the invention can comprise one or more isolated strains of *S. uberis*, for example, ATCC 13386, ATCC 13387, ATCC 19435, ATCC 27958, ATCC 35648, ATCC 700407, ATCC 9927, strain KJ2 or strain KJ2sm. KJ2sm is a naturally occurring genetic variant of KJ2 that is resistant to 1 mg/ml streptomycin and provides the same advantages as for streptomycin-resistant strains of *S. oralis*. One or more isolated strains of *S. oralis* or one or more isolated strains of *S. uberis*, or both, can be used in compositions and methods of the invention.

Compositions of the invention can comprise one or more isolated *mutans streptococcus* bacteria species deficient in the production of lactic acid. These species include, for example, *S. rattus, S. cricetus, S. mutans, S. sobrinus, S. downeii, S. macacae*, and *S. ferus*. A *mutans streptococcus* of the invention does not substantially produce L(+) lactate dehydrogenase (LDH). Such a strain is termed an LDH-deficient strain. An LDH-deficient strain of *mutans streptococcus* produces 25%, 20%, 10%, 5%, 2%, 1%, or less than 1% of the lactic acid produced by wild-type strains of *mutans streptococcus* under similar conditions. An LDH-deficient *mutans streptococcus* strain can be a naturally occurring strain of *mutans streptococcus* or a genetically modified strain of *mutans streptococcus*. LDH-deficient *mutans streptococcus* can compete with and/or displace pathogenic bacteria such as *S. mutans*, a principal etiological agent of dental caries, in the oral cavity. LDH-deficient *mutans streptococcus* stains will compete with *S. mutans* for the same nutrients, colonization sites, etc. Therefore, LDH-deficient *mutans streptococcus* strains can be used to, for example, prevent and/or treat dental caries. LDH-deficient strains of *mutans streptococcus* are non-pathogenic, alter the microenvironment of the oral cavity to prevent colonization or outgrowth of pathogenic organisms, and/or displace pathogenic organisms from the oral cavity where the pathogen is part of the host's indigenous flora.

Examples of LDH-deficient *mutans streptococcus* strains include, for example, *S. rattus* JH145 (ATCC 31377) (a spontaneous, naturally-occurring LDH-deficient mutant) and JH140 (ATCC 31341) (a chemically-modified LDH-deficient mutant). See e.g., Stanshenko & Hillman, Microflora of plaque in rats following infection with an LDH-deficient mutant of *Streptococcus rattus*, Caries Res. 23:375-377 (1989); Hillman, Lactate dehydrogenase mutants of *Streptococcus mutans*: Isolation and preliminary characterization. Infect. Immun. 21:206-212 (1978); see also Abhyankar et al., Serotype c *Streptococcus mutans* mutatable to lactate dehydrogenase deficiency. J. Dent. Res. 64:1267-71 (1985).

An LDH-deficient strain of *mutans streptococcus* can be derived from a *mutans streptococcus* strain using, for example, chemical or physical mutagenesis techniques. Strains that are mutagenized using these techniques are considered genetically modified strains. For example, a *mutans streptococcus* strain can be subjected to mutagens such as nitrous acid, formic acid, sodium bisulphate, UV light, base analog mutagens, including for example, 5-bromo-deoxyuridine (5BU), alkylators such as ethyl methane sulfonate (EMS), methyl methane sulfonate (MMS), diethylsulfate (DES), and nitrosoguanidine (NTG, NG, MNNG). See e.g., In Vitro Mutagenesis Protocols, Braman, Ed., Humana Press, 2002.

Naturally-occurring, spontaneous LDH-deficient *mutans streptococcus* strains can be prepared using methods disclosed in, for example, Hillman, Lactate dehydrogenase mutants of *Streptococcus mutans*: isolation and preliminary characterization. Infect. Immun. 21:206-212 (1978). Spontaneous LDH-deficient mutants occur at the rate of approximately 10-5 frequency. See Johnson et al., Cariogenic potential in vitro in man and in vivo in the rat of lactate dehydrogenase mutants of *Streptococcus mutans*. Arch. Oral Biol. 25:707-713 (1980).

Naturally-occurring, spontaneous LDH-deficient strains of *mutans streptococcus* can be differentiated from LDH-producing strains of *mutans streptococcus* by plating the bacteria on glucose tetrazolium medium. LDH-deficient *mutans streptococcus* colonies will be bright red and relatively larger in size than colonies of the parent strain, which are white and relatively smaller in size on the glucose tetrazolium medium. Naturally-occurring, spontaneous LDH-deficient strains of *mutans streptococcus* can be used in a composition of the invention.

An LDH-deficient strain of *S. rattus* has been isolated. Briefly, a culture of *S. rattus* BHT-2 was grown overnight to saturation in Todd Hewitt broth, and diluted samples were spread on glucose tetrazolium medium to give approximately 300 colonies per plate. Wild-type, acid producing colonies are white on this medium. LDH-deficient mutants are bright red. *S. rattus* JH145 was one red colony amid approximately 100,000 white colonies that were screened. *S. rattus* JH145 is therefore a naturally-occurring, LDH-deficient mutant.

LDH-deficient strains of *mutans streptococcus*, such as LDH-deficient mutants of *S. rattus* BHT-2, produce less total titratable acid when incubated in the presence of glucose and other sugars or polyols, make substantially less lactic acid when incubated in the presence of glucose in the case of resting and growing cultures, adhere better to hydroxyapatite and accumulate more plaque when grown in the presence of sucrose. LDH activity can be assayed as described by Brown & Wittenberger (J. Bacteriol. 110:604, 1972).

Terminal pH can be determined by subculturing strains (1:100) in Todd-Hewitt broth containing 1% glucose. After 48 hours incubation in candle jars at 370 C, the absorbance at 580 nm and pH of the cultures can be determined. Lactic acid concentration of cultures can be determined by gas-liquid chromatography. See Salanitro & Muirhead, Quantitative method for the gas chromatographic analysis of short-chain monocarboxylic and dicarboxylic acids in fermentation media. Appl. Microbiol. 29:374-381 (1975); Hillman et al., Acetoin production by wild-type strains and a lactate dehydrogenase-deficient mutant of *Streptococcus mutans*. Infect. Immun. 55:1399-1402 (1987). Additionally, any genetic modification techniques known to those of skill in the art can be used to create an LDH-deficient *mutans streptococcus* strain from an LDH-producing *mutans streptococcus* parent strain. For example, an LDH gene or a portion of an LDH gene can be deleted or mutagenized, including, for example, insertional mutagenesis techniques. Other mutagenesis techniques include, for example, homologous recombination, recursive sequence recombination, oligonucleotide-directed mutagenesis, site-directed mutagenesis, error-prone PCR, phosphothioate-modified DNA mutagenesis, uracil-containing template mutagenesis, gapped duplex mutagenesis, point mismatch repair mutagenesis, repair-deficient host strain mutagenesis, radiogenic mutagenesis, deletion mutagenesis, restriction-selection mutagenesis, restriction-purification mutagenesis, site saturation mutagenesis, ensemble mutagenesis, recursive ensemble mutagenesis, and chimeric nucleic acid creation. Therefore, any genetic modification technique that disables an LDH gene can be used to produce an LDH-deficient *mutans streptococcus* strain. In one embodiment of the invention, the LDH-deficient strains, whether naturally-occurring or genetically-modified mutants, have a reversion frequency less than 10-7 and produce less than about 10% of the parental level of lactate dehydrogenase activity.

The use of two or more different species of bacteria can provide an advantage over using a single species. This is because different species of bacteria colonize different surfaces or portions of teeth. Therefore, the use of more than one species of bacteria can be used to occupy all or most surfaces of the teeth, whereas the use of only one species of bacteria may result in certain surfaces or portions of the teeth being uncolonized. Therefore, all surfaces of the teeth are exposed to whitening action.

Compositions of the invention can further comprise one or more carbon sources that are metabolizable by the one or more isolated, non-pathogenic, hydrogen peroxide-producing bacterial species or strains or the one or more lactate dehydrogenase deficient *mutans Streptococcus* species or strains or both types of species or strains. Carbons sources include, but are not limited to, for example, glucose, sorbitol, mannitol, fructose, galactose, maltose, sucrose, xylose, lactose, glycerol or combinations thereof.

The compositions of the invention can include a pharmaceutically acceptable or nutritionally acceptable carrier. The carrier is physiologically compatible with the oral cavity of the subject to which it is administered. Carriers can be solid-based, dry or at least partially low water activity materials suitable for formulation into tablet, capsule, lozenge, and/or powdered form. A carrier can also be a liquid or gel-based materials, for formulations into liquid, gel, and/or chewing gum forms. Suitable liquid or gel-based carriers include but are not limited to: water, physiological salt solutions, urea, alcohols and derivatives, and glycols (e.g. ethylene glycol or propylene glycol). The composition of the carrier can be varied so long as it does not interfere significantly with the therapeutic activity of the bacterial strains of the invention.

In other embodiments the carrier can be in the form of an oral patch. Such an oral patch can include stabilized beneficial bacteria and an adhering surface that at least temporarily attaches to a surface of the oral cavity (for example the hard palate, soft palate, gums, and/or tooth surfaces) and maintains the position of the patch within the oral cavity following application and a protective surface. The protective surface can be at least partially permeable to saliva, and serves to release the stabilized bacteria over time following application. An oral patch of the inventive concept can release stabilized beneficial bacteria for from 1 minute to 20 minutes or more following application, thereby supporting colonization of the oral cavity by the released bacteria rather than simple transfer to the lower digestive tract. For example, in some embodiments the protective surface can be porous, where the pores are dimensioned to release bacteria into the oral cavity. Such pores can range in size from greater than 0.02 μm in diameter to up to about 2 mm in diameter. In such an embodiment the patch can be provided with pores that are occupied by a substance that dissolves in the oral cavity, such as a water soluble material or a starch-based material that is broken down by salivary amylase.

In some embodiments such a patch is applied to a surface of the oral cavity and allowed to adhere, then left in place for a prescribed period of time (for example, about 10 seconds to about 20 minutes) before being removed. In other embodiments the protective surface can be dissolvable within the oral cavity, for example by being at least partially water soluble and/or including a starch component degradable by oral amylase. In such an embodiment the protective surface can be formulated to remain at least partially intact through a prescribed treatment period (for example, from about 10 seconds to about 20 minutes). In some embodiments the patch can include an adhesive that aids in adherence to a surface of the oral cavity. In other embodiments the patch can not include such an adhesive, and rely on taction to remain in place.

In some embodiments a composition of the inventive concept can be formulated to be suitable for oral administration as a consumable substance in a variety of ways, for example in a solid, semi-solid, liquid (including, e.g. a viscous liquid, a paste, a gel, or a solution), a dried mass, a dentifrice, a mouth wash, an oral rinse, a liquid suspension, a topical agent, a powdered food supplement, a paste, a gel, a solid food, an oral rinse, a packaged food, a wafer, lozenge, chewing gum and the like. Other formulations will be readily apparent to one skilled in the art. A composition of the invention can include a nutrient supplement component and can include any of a variety of nutritional agents, as are well known, including vitamins, minerals, essential and non-essential amino acids, carbohydrates, lipids, foodstuffs, dietary supplements, and the like.

In a preferred embodiment of the inventive concept the composition is provided as a food, which is placed in the mouth and chewed for a period of time prior to swallowing. Such chewing can serve to expose the stabilized bacterial preparation of the composition and rehydrate it, while distributing it throughout the oral cavity for a period of time sufficient to establish at least transient colonization by the bacteria. This can be accomplished by using a single portion that is retained in the mouth (for example, a chewing gum) and/or by providing multiple "bites" that are consumed over time (for example, a food or candy bar). Suitable times for establishing at least transient colonization of the oral cavity are for about 30 seconds, about 45 seconds, about 1 minute, about 90 seconds, about 2 minutes, about 3 minutes, about 4 minutes, about 5 minutes, or more than about 5 minutes. Such times can be a time through which a single portion is held in the mouth, or can be a summation of times during which different portions are held in the mouth during consumption.

Compositions of the invention can also include natural or synthetic flavorings and food-quality coloring agents, all of which are compatible with maintaining viability of the bacterial species or strains of the invention.

A composition of the invention can include one or more gelling agents that can act as an adhesive agent to adhere the composition to the teeth. The concentration of the gelling agent may be greater than about 2, 4, 6, 8, 10, 15, 20, 30, 40, 50, 60, 70, 80 or less than about 80, 70, 60, 50, 40, 30, or 20 percent by weight of the composition.

Suitable gelling agents and adhesion agents useful in the present invention include, for example, silicone, polyethylene oxide, polyvinyl alcohol, poly alkyl vinyl ether-maleic acid copolymer (PVM/MA copolymer) such as, Gantrez A N 119, AN 139, and S-97, polyvinyl alcohol, polyacrylic acid, Poloxamer 407 (Pluronic), polyvinyl pyrrolidone-vinyl acetate copolymer (PVP/VA copolymer), such as Luviskol VA, and Plasdone S PVP/VA, polyvinyl pyrrolidone (PVP, e.g., K-15 to K-120), Polyquaterium-11 (Gafquat 755N), Polyquaterium-39 (Merquat plus 3330), carbomer or carboxypolymethylene (Carbopol), hydroxy propyl methyl cellulose, hydroxy ethyl cellulose, hydroxy propyl cellulose, corn starch, carboxymethyl cellulose, gelatin and alginate salt such as sodium alginate, natural gums such as gum karaya, xanthan gum, Guar gum, gum arabic, gum tragacanth, and mixtures thereof.

A humectant or plasticizer can be present in compositions of the invention. Humectants or plasticizers include, for example, glycerin, glycerol, sorbitol, polyethylene glycol, propylene glycol, and other edible polyhydric alcohols. The humectants or plasticizers can be present between at about 1% to about 99%, about 10% to about 95%, or at between about 50% and about 80% (or any range between 1% and 99%) by weight of a composition.

Bacteria of the invention can be prepared for use in a fermentor or similar culture vessel. The bacteria can be harvested from the fermenter and further processed (for example, concentrated) for stability or as part of a process that confers stability under storage conditions. Bacterial preparations can be considered stable if they provide sufficient viable bacteria for their intended use after at least 6 months of storage at ambient or reduced (for example, down to 2-8° C., 0° C., or −20° C.). Bacteria of the invention can be stabilized by drying, for example, dehydration, lyophilization, and/or spray drying. Spray drying generally comprises spraying a suspension of bacteria in a vessel and under a steam of hot air. Such drying can be performed in the presence of compounds that improve viability following drying, such as trehalose and/or other stabilizing carbohydrates, serum albumin, ovalbumin, etc. As noted above, such dried bacterial preparations can be further protected by suspension in a water-immiscible fluid, such as an edible oil. Bacteria can also be stabilized for use by microencapsulation (see e.g. U.S. Pat. No. 6,251,478), freeze-drying, or by coating with a protective substance such as, for example, lipid material such as triacylglycerols, waxes, organic esters, soybean oil, cottonseed oil, palm kernel oil, and esters of long-chain fatty acids and alcohols.

The invention provides methods for delivering a composition that provides probiotic bacteria that can at least transiently colonize the oral cavity, by the providing a food substance that includes a stabilized form of the probiotic bacteria. Consumption of the food substance provides a bolus of the probiotic bacteria, and does so over a period of time (e.g. from 10 seconds to 30 minutes) the permits said bacteria to adhere to one or more surfaces of the oral cavity of the consumer. In competing for other bacteria within this limited environment one or more oral care benefits can be realized. In some embodiments one or more bacterial strains within the probiotic bacteria population can elaborate compounds (such as peroxides) that provide additional benefits, including a reduction in discoloration in tooth enamel.

The bacterial species or strains can be present in a composition of the invention in an amount effective to provide sufficient viable bacteria for at least transient colonization of the oral cavity. As noted above, displacement of existing bacterial population within the mouth by bacteria of the probiotic bacteria mixture can reduce, prevent and/or ameliorate unwanted effects that resulted from the presence of the existing bacteria population. Such unwanted effects include symptoms of dental caries, periodontitis, bacterial infections or diseases, oral wounds, *Candida* or fungal overgrowth, halitosis, or xerostomia-induced dental caries or periodontal disease or to alleviate, reduce, prevent, or ameliorate stains or discoloration on the teeth either permanently or temporarily.

An effective amount is an amount of a composition of the invention that is sufficient to provide the desired colonization, but low enough to avoid serious negative effects (at a reasonable benefit/risk ratio). The effective amount of a composition of the invention may vary with the particular native bacteria population present, with negative effects present in the oral cavity due to the presence of this native bacteria population, the age and physical condition of the patient being treated, the duration of over which the probiotic bacteria will be used, the nature of any concurrent medical interventions, the specific form of the food source employed, and the particular vehicle from which the probiotic bacteria composition is applied.

The VITA 3D Master™ Shade Guide provides a range of tooth shades that varies from very light to very dark. A total of 29 tooth shades constitute the entire range of colors between these two endpoints on a scale of brightness. In one embodiment of the invention, methods of the invention provide a change of about 1, 2, 3, 4, 5, 6, 7, 8, 9, 10, 11, 12, 13, 14, 15 or more (or any value or range in between 1 and 29) VITA 3D Master™ shades of brightness.

The inventive concept provides compositions and methods in which a preparation of dried, lyophilized, or otherwise bacteria useful in a probiotic mixture are introduced to the oral cavity through the use of a food or similar solid or semi-solid consumable. Such bacteria can include lactate dehydrogenase-deficient *mutans streptococcus* strains, for example *mutans streptococcus* that has been exposed to mutagens or genetically engineered to show reduced or absent lactate dehydrogenase activity. Alternatively or in addition, such bacteria can include bacterial strains that generate hydrogen peroxide in the oral cavity. As opposed to protecting such compositions for release in the gut (e.g. stomach, small intestine, large intestine), compositions and methods of the inventive concept provide protection and stabilization of such dried or lyophilized bacterial preparation during storage, and release a significant portion of the dried or lyophilized bacterial preparation while in the oral cavity (preferably over a period of time of up to 15 minutes). For example, up to about 25%, 30%, 35%, 40%, 50%, 55%, 60%, 65%, 70%, 75%, 80%, 85%, 90%, 95%, or greater than about 95% of the total bacterial content of a composition of the inventive concept can be exposed to the interior of the oral cavity of a user during normal consumption (e.g.

excluding circumstances where a food substance intended for chewing or sucking is immediately swallowed intact).

Embodiments of the inventive concept can include bacterial preparations that are useful in colonizing an oral cavity and displacing potentially harmful native bacteria, but whose use is hampered by a relative lack of stability and/or viability upon storage under conventional conditions (i.e. labile bacteria). In some embodiments simple drying or lyophilization does not provide suitable stability (for example, for at least 12 months) for labile bacteria under storage conditions. Suitable storage conditions include storage at 2° C. to 8° C. (e.g. conventional refrigeration), storage at 15° C. to 25° C. (e.g. "room" temperature) under low to near-saturating humidity conditions. In some embodiments additional packaging is provided in the form of a wrapper or other sealed enclosure that surrounds the foodstuff. Such a wrapper or sealed enclosure can provide a moisture barrier, and in some embodiments can additionally enclose a dessicating agent (e.g. silica gel). In some embodiments such a wrapper or sealed enclosure can be sparged or otherwise filled with a non-reactive gas (e.g. N2, Ar, CO2) prior to sealing. While such a wrapper or sealed enclosure can provide protection of the labile bacterial preparation, preferred embodiments of the inventive concept can include additional protective features, such as coating, encapsulations, etc. These can be useful in extending the useful life of the labile bacterial preparation, particularly on extended storage or on partial consumption of the foodstuff. In some embodiments such additional protective features can provide sufficient protection that a wrapper or sealed enclosure is not necessary.

In some embodiments of the inventive concept the labile bacterial preparation can be provided as a dried and/or lyophilized preparation, for example as a powder or granules. In such an embodiment lyophilization or drying can be performed in the presence of stabilizing agents that act to extend the useful lifetime of the labile dried bacteria, thereby incorporating such stabilizing agents into the powder or granules. In other embodiments such stabilizing agents can be provided in or as part of a matrix, in which the dried or lyophilized bacterial preparation is imbedded or suspended in the form of particles of powder, individual granules, etc. Suitable stabilizers include proteins (e.g. albumin, mammalian gelatin, teleost gelatin, milk solids, serum products, etc.), free radical inhibitors, reducing agents, sugars or sugar polymers (e.g. glucose, trehalose, sucrose, sorbitol, mannitol, dextran, cyclodextrin, etc.), amino acids (e.g. glycine), surfactants (e.g. polysorbate 20, polysorbate 80) and/or synthetic polymers (e.g. polyvinylpyrrolidone).

In some embodiments, as shown in FIG. 1A, a food composition includes a matrix 100 having one or more stabilized bacterial inclusion(s) 110, and can be provided with a protective shell or capsule 120. In some embodiments such a protective shell can be dimensioned (e.g. 1 mm to 20 mm in a given linear dimension) and have a thickness (e.g. 0.05 mm to 2 mm) that permits the shell 120 to be ruptured during normal chewing. For example, such an embodiment could be provided in the form of edible "sprinkles", such as are used in food decoration, or as a candy or lozenge (or a component of same). In some embodiments the protective shell or capsule 120 can be composed of a material that offers moisture resistance but that is degraded by or soluble in substances found in the mouth (such as saliva or components thereof). For example, such a shell can be at least partially water soluble, and/or include a starch or starch-polymer component that is reactive with the amylase found in saliva. In such an embodiment the shell or capsule 120 would provide protection until entered into the oral environment, then degrade and release the stabilized bacteria 110.

Figure 1B:
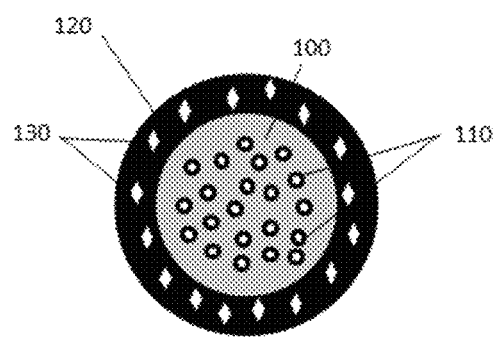

In some embodiments, as shown in FIG. 1B, such a shell 120 can incorporate one or more reactive inclusion(s) 130 that are stable under storage conditions but that disrupt the integrity when of the shell 120 when exposed to the oral environment. Such reactive inclusions 130 can, for example, rapidly dissolve (e.g. less than 5 minutes) in the oral environment, thereby weakening the shell 120 and exposing the interior contents. Alternatively, such reactive inclusion 130 can react with components of the oral cavity to generate gases that pressurize and disrupt the shell 120. Suitable reactive inclusion 130 include, for example, mixtures of an edible organic acid (e.g. ascorbic acid, malic acid, etc.) and a carbonate or bicarbonate salt (e.g. $CaCO_3$, $Na_2CO_3$, $NaHCO_3$, etc.). Exposure of such a mixture to aqueous solutions (such as saliva) can result in dissolution of the reactive inclusion and rapid generation of $CO_2$ gas. The resulting loss in the integrity of the shell 120 can lead to release of the stabilized bacteria 110 into the oral cavity over time (e.g. from 1 second to 10 minutes).

Figure 2:
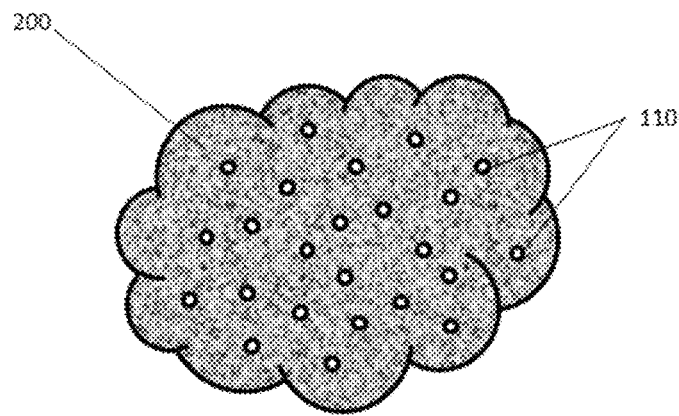
FIG. 2 schematically depicts an embodiment in which a stabilized bacterial preparation is provided in a foam or gel.

In other embodiments, as shown in FIG. 2, inclusions of stabilized bacteria 110 are provided in a stiff (i.e. non-conforming to a container's shape) low water activity, disruptable foam or gel 200 that is loses structural integrity within the oral cavity. In some embodiments such a foam, gel, and/or aerogel 200 can include stabilizers, coloring agents, and/or flavorants. Loss of structural integrity can be due to factors such as solubility and/or degradation of one or more components of the foam. In some embodiments loss of structural integrity can be provided by mechanical disruption within the mouth, for example by chewing. Such a stiff foam, stiff gel, and/or dry foam (e.g. aerogel) carrying inclusions of dried or lyophilized bacteria can be produced in bulk and then trimmed to a desirable size and/or shape, such as a size and shape suitable for inclusion in a breakfast cereal, inclusion in food bar, as a chewing gum, etc. In such an embodiment stabilized bacteria near the periphery may be more susceptible to environmental factors while those towards the center remain protected. Suitable components for such a disruptable foam, gel, and/or aerogel include edible starches, edible proteins (such as gelatin), and/or edible gums (such as xanthan gum). In some embodiments, the foam, gel, and/or aerogel can be produced as a wet foam or gel that includes probiotic bacteria suitable for at least transiently colonizing the oral cavity and dried or lyophilized to provide a low moisture, disruptable material and a lyophilized or dried bacterial preparation in the same process step.

Figure 3:
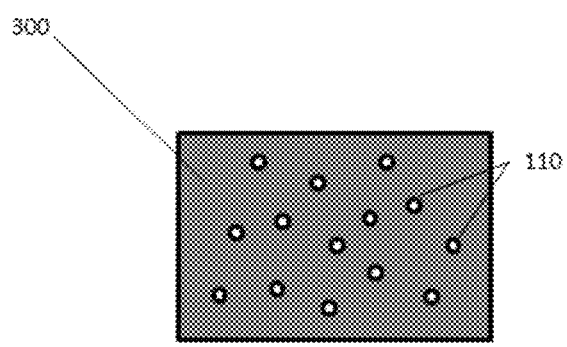
FIG. 3 schematically depicts an embodiment in which a stabilized bacterial preparation is provided in a homogeneous matrix.

In another embodiment of the inventive concept, as shown in FIG. 3, inclusions of dried or lyophilized bacteria 110 are provided in a low-melting point (e.g. less than or equal to about 45° C.) matrix 300. For example, such a matrix can have a melting point that is within 5° C. of body temperature within an oral cavity. Introduction into the oral cavity results in melting of the low-melting point matrix, which in turn releases the stabilized bacteria inclusions 110 into the oral cavity. In a preferred embodiment, the low-melting point matrix is selected to have a melting point temperature that is tolerated by the dried or lyophilized bacteria for from 5 minutes to 1 hour, thereby permitting formulation through simple addition of the dried or lyophilized bacteria to the melted low-melting point matrix. Suitable low-melting point matrices include edible oils and/or waxes, such as dairy butter, lard, margarine, mutton tallow, coconut oil, cocoa butter, milk fat, palm kernel oil, and/or palm oil. Such a low-melting point matrix carrying inclusions of stabilized bacteria can, for example, form at least part of a food bar, decorative frosting, pastry filling, and/or confection.

In some embodiments stabilized bacteria can be provided as a suspension in an edible oil that is liquid at ambient temperature, or that becomes liquid as it approaches body temperature (i.e. 37° C.). Such an oil suspension can be provided as a liquid, gel, and/or paste inclusion (e.g. creamy filling) of a food or confection, such that it is surrounded by a conventional foodstuff. For example, such an oil suspension can be provided as a liquid center of a gum, lozenge, or candy, such that the bacterial suspension is released into the mouth on chewing. Similarly, such a gel or paste can be incorporated into a filling of a pastry or similar foodstuff. In a preferred embodiment such an oil suspension can include a flavorant (e.g. a sweetener or other flavor). Suitable edible oils include coconut oil, corn oil, cottonseed oil, olive oil, palm oil, peanut oil, canola/rapeseed oil, safflower oil, sesame oil, soybean oil, and/or sunflower oil.

One embodiment of the invention provides a method of non-persistently colonizing an oral cavity of a subject with therapeutically-effective bacteria comprising providing a subject with a food item as described above, wherein the subject exposes the food item to their oral cavity by consumption. In one embodiment of the invention the administered bacterial strains do not permanently colonize the oral cavity, rather the strains are present in the oral cavity for about 1 day, about 1 week, about 2 weeks, about 3 weeks, about 1 month, about 3 months or about 12 months after administration of the bacteria.

Compositions of the invention can be administered at a dose of about $1\times10^3$, $1\times10^5$, $1\times10^7$, $1\times10^9$, or $1\times10^{11}$ CFU (or any range or value between about $1\times10^3$ and about $1\times10^{11}$) of viable bacteria. A dose of a composition of the invention can be administered at three times a day, twice a day, once a day, every other day, two times a week, weekly, biweekly, or monthly. One, two, or more doses of a composition of the invention can be administered per day for about 1 week, about 2 weeks, about 1 month, about 2 months, about 3 months, about a year or more.

Compositions of the invention can be used daily as part of an oral care regimen. Using compositions of the invention as part of a daily oral care regimen allows a user to achieve and sustain a variety of desired oral care benefits, including but not limited to white, tartar-free teeth.

A kit of the invention can contain a one month, two month, three month, four month, five month, six month, or 12 month supply of a composition of the invention. Such a kit can include instructions for use of the enclosed food item. A composition of the invention can be packaged individually within the kit. Alternatively, a plurality of the packaged compositions can be provided in a storage container or outer package or carton. In some embodiments a kit can include an additional component that aids in product stability, for example a dessicant or oxygen-consuming material (for example, within individual packaging or within a container including multiple food items).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of at least transiently colonizing an oral cavity with probiotic bacteria, comprising:
    providing an oral patch comprising a protective layer, and a film layer comprising a first surface coupled to the protective layer, and wherein the film layer comprises a stabilized bacterial formulation comprising an isolated, non-pathogenic, hydrogen peroxide bacterial species or strain and a genetically modified LDH-deficient bacterial strain, wherein the protective layer is permeable;
    placing the film layer in contact with a surface of the oral cavity; and
    retaining the oral patch in the oral cavity for a time sufficient to release at least a portion of the stabilized bacterial formulation into the oral cavity.

2. The method of claim 1, wherein the protective layer is porous.

3. The method of claim 1, wherein the stabilized bacterial formulation comprises lyophilized bacteria.

4. The method of claim 1, wherein the stabilized bacterial formulation comprises an encapsulated bacteria.

5. The method of claim 1, wherein the encapsulated bacteria comprises a matrix compound selected from the group consisting of casein, starch, a chitosan, and an edible wax or oil.

6. The method of claim 5, wherein the edible wax or oil has a melting point of greater than 35° C.

* * * * *